United States Patent [19]

Muchowski et al.

[11] Patent Number: 4,532,138
[45] Date of Patent: Jul. 30, 1985

[54] THIAZOLIDIN-2-ONE ANALOGS

[75] Inventors: Joseph M. Muchowski, Sunnyvale, Calif.; Angel Guzman, Mexico City, Mexico

[73] Assignee: Syntex (U.S.A.) Inc., Palo Alto, Calif.

[21] Appl. No.: 528,494

[22] Filed: Nov. 2, 1983

Related U.S. Application Data

[63] Continuation of Ser. No. 323,152, Nov. 20, 1981, Pat. No. 4,410,526.

[51] Int. Cl.³ ................ C07D 277/10; A61K 31/425
[52] U.S. Cl. .................................... 514/369; 548/187
[58] Field of Search ....................... 548/187; 424/270

[56] References Cited

U.S. PATENT DOCUMENTS 4,022,794  5/1977  Smith et al. ..................... 548/187
4,059,587  11/1977  Smith et al. ..................... 548/187

*Primary Examiner*—Donald G. Daus
*Assistant Examiner*—S. A. Gibson
*Attorney, Agent, or Firm*—Ellen J. Buckles; Tom M. Moran; Alan M. Krubiner

[57] ABSTRACT

Compounds of the formula:

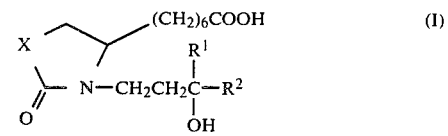

and the pharmaceutically acceptable, non-toxic salts and esters (alkyl, 1–6C) thereof, wherein:
X is O or S;
$R^1$ is selected from the group consisting of:
(a) alkyl or cycloalkyl of 3–8 carbons,
(b)

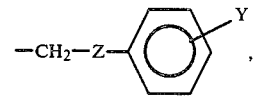

in which Z is O, S or —$CH_2$, and Y is lower alkyl (1–4C), lower alkoxy (1–4C), halo, or —$CF_3$, and
(c)

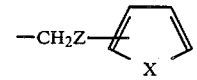

in which Z and X are as herein defined; and
$R^2$ is hydrogen or methyl;
exhibit prostaglandin-like activity and are, thus, useful as platelet aggregation inhibitors.

6 Claims, No Drawings

THIAZOLIDIN-2-ONE ANALOGS

This is a continuation of application Ser. No. 323,152 filed Nov. 20, 1981, now U.S. Pat. No. 4,410,526.

BACKGROUND OF THE INVENTION

The present invention relates to prostaglandin analogs which are platelet aggregation inhibitors. In particular, heterocyclic oxazolidinone and thiazolidinone analogs are thus useful.

A number of classes of compounds have been shown to be platelet aggregation inhibitors in vitro. Prostaglandins and their analogs, different in structure from those of the invention herein, cyclooxygenase inhibitors, phosphodiesterase inhibitors, and membrane active compounds are examples of classes whose mechanism of action is understood. In addition, a class of miscellaneous compounds, whose mechanism of action is not known, including, for example, ticlopidine and adenosine, has also been used. Although the above compounds are active in vitro and in some animal model systems, there is, at the present time, no compound clinically verified to inhibit platelet aggregation in human beings, with the exception of aspirin for use in prevention of stroke (prior to any history thereof) in males.

Therefore, there remains a need for a satisfactory clinically usable platelet aggregation inhibitor. The compounds of the present invention are analogs of prostaglandins. Prostaglandins are a class of naturally occurring $C_{20}$ fatty acids which are derived from three fatty acids essential to the human diet. A number of natural prostaglandins are known which are variations on the general structure

[structure of prostaglandin skeleton with positions 3, 5, 7, 9, 11, 13, 15, 17, 19 and COOH group]

in which the cyclopentane ring is oxidized, and a hydroxyl group appears in the $C_{12}$ to $C_{20}$ side chain.

Compounds known in the art which are closest in structure to those of the present invention are those prostaglandin analogs found in U.S. Pat. Nos. 4,059,587 and 4,102,888 which disclose heterocyclic forms of prostaglandins having different ring systems from those of the present invention.

SUMMARY OF THE INVENTION

The present invention, in one aspect, relates to compounds of the formula:

[structure showing ring with X, N, O and substituent (CH₂)₆COOH, with N—CH₂CH₂C(R¹)(R²)(OH)]  (I)

and the pharmaceutically acceptable, non-toxic salts and esters (alkyl, 1-6C) thereof, wherein:
X is O or S;
R¹ is selected from the group consisting of:
 (a) alkyl or cycloalkyl of 3-8 carbons,
 (b)

[—CH₂—Z—(phenyl)—Y], in which Z is O, S or —CH₂, and Y is lower alkyl (1-4C), lower alkoxy (1-4C), halo, or —CF₃, and
 (c)

[—CH₂Z—(heterocycle with X)]

in which Z and X are as herein defined; and
$R^2$ is hydrogen or methyl.

In another two aspects, the invention concerns pharmaceutical compositions containing a compound of Formula I and to methods of inhibiting blood platelet aggregation utilizing compounds of formula I or the aforesaid composition. Finally, the invention also relates to a process for the preparation of compounds of formula I.

DETAILED DESCRIPTION OF THE INVENTION

Definitions

As used herein, "lower alkyl" means a branched or unbranched saturated hydrocarbon chain of 1-4 carbons, such as, for example, methyl, ethyl, n-propyl, i-butyl and the like.

"Lower alkoxy" means the group —OR wherein R is lower alkyl as herein defined.

"Alkyl" means a branched or unbranched saturated hydrocarbon chain containing 1-6 carbon atoms, such as methyl, ethyl, propyl, tert-butyl, n-hexyl and the like.

The compounds of the invention will be named systematically herein as substituted oxazolidin-2-ones or thiazolidin-2-ones, with the heterocyclic ring numbered as shown:

[ring structure with positions labeled 1 (X), 2 (=O), 3 (N), 4, 5]

"Pharmaceutically acceptable, non-toxic salts and esters" refers to salts derived from pharmaceutically acceptable non-toxic inorganic and organic bases, and alkyl esters derived from hydrocarbons of branched or straight chain, having from 1 to 6 carbon atoms, respectively.

Salts derived from inorganic bases include sodium, potassium, lithium, ammonium, calcium, magnesium, ferrous, zinc, copper, manganous, aluminum, ferric, salts and the like. Particularly preferred are the ammonium, potassium, sodium, calcium and magnesium salts. Salts derived from pharmaceutically acceptable organic non-toxic bases include salts of primary, secondary and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, choline and caffeine.

Typical alkyl ester groups are, for example, methyl, ethyl, propyl, isopropyl, butyl, t-butyl, isoamyl, pentyl, isopentyl, and hexyl.

Preparation Methods

The compounds of formula I are prepared according to Reaction Scheme 1:

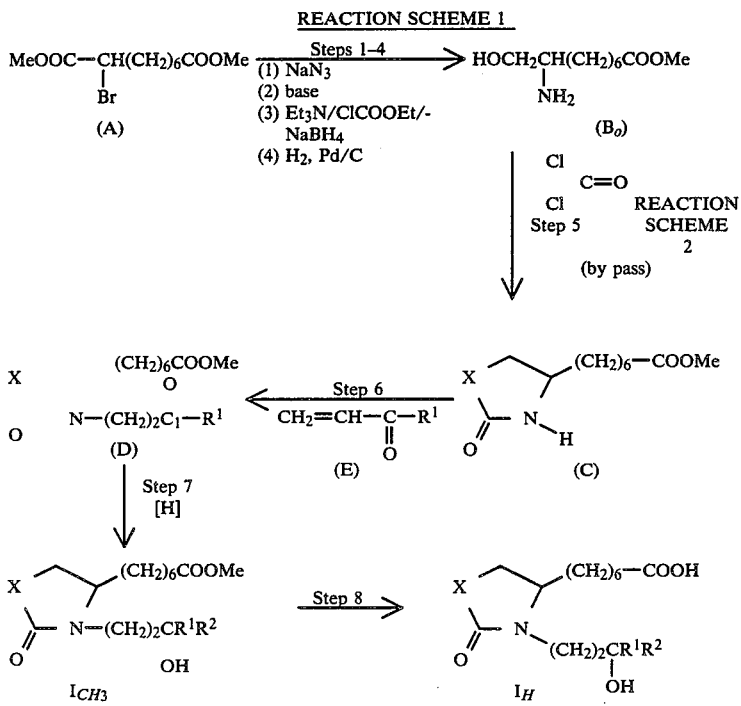

Reaction Scheme 1, above, shows the preparation of two specific forms of the compounds of formula I—that is the methylester and the free carboxylic acid, formulas $I_{CH_3}$ and $I_H$ respectively. It is understood, of course, that the compound of formula $I_H$ may be converted into the pharmaceutically acceptable non-toxic salts and esters of the carboxylic acid moiety using conventional means.

The pharmaceutically acceptable non-toxic salt derivatives of the compounds of Formula I are prepared by treating the free acids with an appropriate amount of pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, maganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The reaction is conducted in water, alone or in combination with an inert, water-miscible organic solvent, at a temperature of from about 0° C. to about 100° C., preferably at room temperature. Typical inert, water-miscible organic solvents include methanol, ethanol, isopropanol, butanol, acetone, dioxane or tetrahydrofuran. The molar ratio of compounds of formula I to base used are chosen to provide the ratio desired for any particular salt. For preparing, for example, the calcium salts or magnesium salts the free acid starting material of formula I can be treated with at least one-half molar equivalent of pharmaceutically acceptable base to yield a neutral salt. When the aluminum salts of the compounds of formula I are prepared, at least one-third molar equivalent of the pharmaceutically acceptable base are employed if a neutral salt product is desired.

The salt derivatives of the compounds of formula I can be reconverted to their respective free acids by acidifying said salts with an acid, preferably an inorganic acid, e.g., hydrochloric acid, sulfuric acid, and the like, at temperature of from about 0° C. to about 50° C., preferably at room temperature.

The pharmaceutically acceptable non-toxic esters of formula I are prepared by esterifying the corresponding free acids with an alcohol reagent corresponding to the desired ester, i.e., are alkanol having up to 6 carbon atoms. This reaction is conducted in the presence of a strong acid, such as boron trifluoride, hydrogen chloride, sulfuric acid, p-toluenesulfonic acid, and the like. Since the alcohol reagent used in the esterification is a liquid at the reaction temperature, the alcohol reagent can be the reaction solvent. Optionally, the reaction can be carried out in an inert organic solvent in which the free acids and the alcohol reagent are soluble, such as a hydrocarbon solvent, e.g., hexane, isooctane, decane, cyclohexane, benzene, toluene, xylene, a halogenated hydrocarbon solvent, e.g., methylene chloride, chloroform, dichlorethane; or an ether solvent, e.g., diethyl ether, dibutyl ether dioxane, tetrahydrofuran, and the like. The reaction is conducted at from about 0° C. to the reflux temperature of the reaction mixture, preferably using hydrogen chloride at a temperature of from 15° C. to about 35° C.

The product is isolated by conventional means such as diluting the reaction mixture with water, extracting the resulting aqueous mixture with a water-immiscible inert organic solvent, such as diethyl ether, benzene, methylene chloride, and the like, combining the extracts, washing the extracts with water to neutrality and then evaporating under reduced pressure.

Typical esters are those ester derivatives prepared from methyl alcohol, ethyl alcohol, propyl alcohol, isopropyl alcohol, butyl alcohol, 2-butyl alcohol, 2-pentyl alcohol, isopentyl alcohol, 2-hexyl alcohol, and the like.

Alternatively, the alkyl esters can be prepared by transesterification, according to methods known in the art. It is preferred in preparing the esters via transesterification to go from a lower ester to a higher ester, e.g., from the methyl ester, for example, to the isoamyl ester, for example. However, by using a substantial excess of a lower alcohol, a higher ester can be transesterified to a lower ester; thus, for example, by using a substantial excess of ethanol, the hexyl ester is converted by the transesterification to the ethyl ester.

In still another alternative, the ester can be prepared by reacting the free acid form with the appropriate diazo alkane, such as diazaomethane, diazo-n-hexane, or diazo-i-propane in an aprotic organic solvent at low temperature.

The reaction sequence in Reaction Scheme 1 is shown starting with the dimethyl ester of α-bromoazelaic acid. However, of course, any other suitable bialkylester of α-bromoazelaic acid could be used. The dimethyl ester, however, is the most readily available, and there is no advantage to using any other derivative. Therefore the dimethyl ester is shown.

The compound of formula A can be prepared by the bromination of a diester of the azelaic acid by means well known in the art. The other "starting" materials of formula E, employed in Step 6 of Reaction Scheme 1, are commercially available compounds.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures could, of course, also be used.

The salt products are also isolated by conventional means. For example, the reaction mixtures may be evaporated to a dryness, and the salts can be further purified by conventional methods.

The compounds of formula I contain two chiral centers, the ring carbon to which the 7-carbon carboxyl containing chain is attached, and the carbon containing the hydroxyl group.

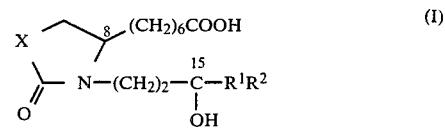

Following the conventional numbering system of prostaglandins; the chiral centers are at carbons 8 and 15.

Accordingly, the compounds of formula I may exist in a total of four stereoisemeric forms. The present invention is intended to include all such forms and mixtures thereof. The end products of Reaction Scheme 1 will be a mixture of all four stereoisemers unless separation is effected. These mixtures may be resolved, if desired, into individual stereoisemers using conventional means as further outlined hereinbelow.

Diastereomers may, of course, be separated by standard techniques for chemical compounds in general, such as fractional crysallization, chromatography, or some combination of these. Ordinarily, such a separation is effected—i.e., into two racemic mixtures: RR/SS and RS/SR. Mixtures of enantiomers may be resolved by converting the compounds of formula I to diastereomeric forms, separating the diastereomers as above, and regenerating compounds of formula I. In the present case, since the compounds are alcohols, a convenient method is to convert them to the diastereomeric esters by reaction with optically active carboxylic acids. The resulting diastereomeric esters may then be separated, and then cleaved, using standard procedures, into the original, but resolved, compounds of formula I.

At the end of Reaction Scheme 1, the resulting compounds of formula I are mixtures of the four stereoisomeric forms, assuming no resolution has been done throughout the procedure. These mixtures may then be separated into a "more polar" and "less polar" form (the racemic mixtures referred to hereinabove) by chromatography. These separated more polar and less polar forms may be tested separately with respect to biological activity. Typically, it is found that the more polar form is more active than the less polar, although both exhibit some activity in vitro with respect to blood platelet aggregation inhibition.

To prepare compounds of formula I wherein X is sulfur, a bypass, which results, in the replacement of O by S in formula C is carried out as represented in Reaction Scheme 2:

REACTION SCHEME 2

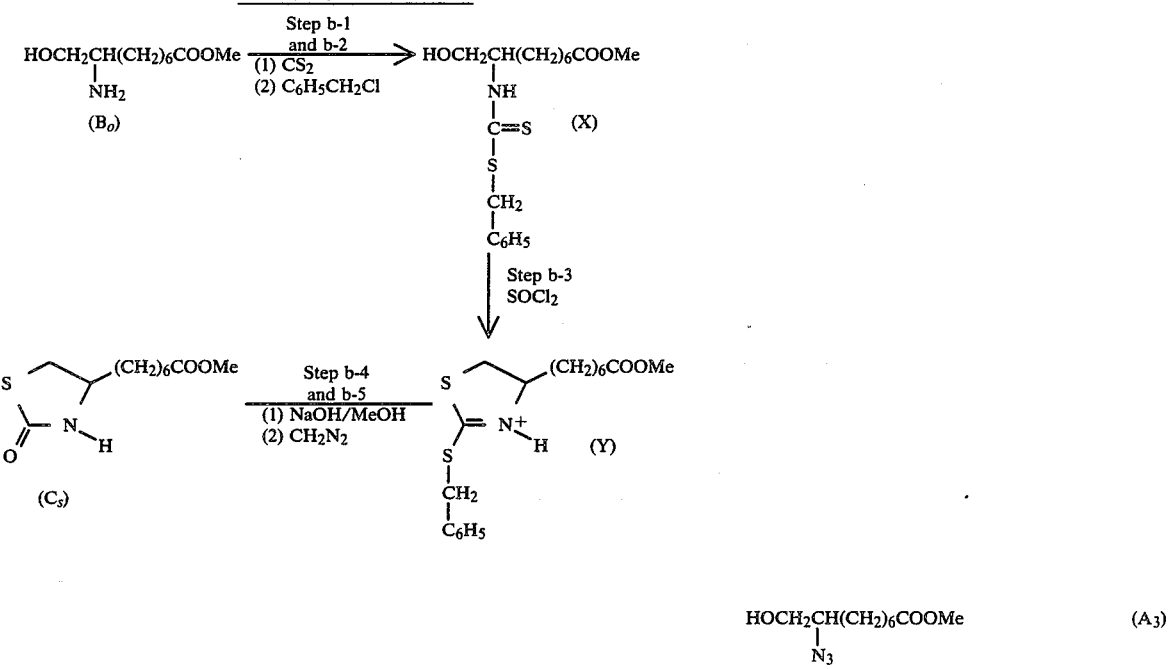

A more detailed summary of general procedures for carrying out Steps 1 through 8 of Reaction Scheme 1 and of Steps b-1 through b-5 of the bypass Reaction Scheme 2 follows:

In Step 1 of Reaction Scheme 1, a large molar excess of sodium azide, preferably a 4 to 5 molar excess, is added to a solution of the compound of formula A in an inert aprotic solvent such as, for example, acetonitrile, or tetrahydrofuran, and the mixture is heated at 50° C. to 120° C., preferably the reflux temperature of the solvent for two to ten hours, preferably three to four hours. The resulting compound of formula $A_1$ is then isolated

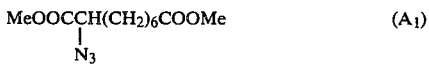

and carried on to Step 2.

In Step 2, the compound of formula $A_1$ is dissolved an aqueous polar organic solvent, such as, for example, aqueous ethanol or methanol, preferably aqueous methanol and a base, such as, for example, sodium hydroxide, potassium carbonate, or sodium carbonate, preferably potassium carbonate, is added in slight excess, preferably a 1.2 to 2 molar excess, with respect to the compound of formula $A_1$. The mixture is then stirred at 5° C. to 30° C., preferably room temperature, for about 1 to 10 hours, preferably for about 3 to 4 hours. The resulting compound of formula $A_2$, which is the corresponding monomethyl ester:

$$HOOC-CH(CH_2)_6COOMe \quad (A_2)$$
$$| $$
$$N_3$$

is isolated by conventional means.

Then, in Step 3, the compound of formula $A_2$ is reduced to the corresponding mono alcohol of formula $A_3$:

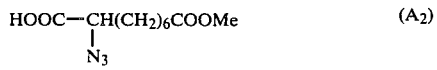

by treatment with a suitable metal hydride.

In conducting Step 3, the compound of formula $A_2$ is treated with a slight molar excess excess of tertiary base, such as, for example, triethylamine in an inert aprotic organic solvent, and cooled to $-0°$ C. to 10° C., preferably 0° C., with stirring. An equi-molar amount (approximately) of a reagent to convert the carboxylic acid to the anhydride, preperatory to its reduction is then added. Ethyl chloroformate is the preferred reagent. The mixture is kept cool for 1 to 2 hours, and filtered for clarification if necessary. The filtrate is then treated with a slight excess of a suitable metal hydride, preferably sodium borohydride, and kept at room temperature for 1 to 6 hours, preferably 2 hours. The compound of formula $A_3$ is then isolated by conventional means.

Finally, in Step 4, the azide is reduced to the amine of formula $B_o$ by treating with hydrogen in the presence of a catalyst. A solution of the compound of formula $A_3$ in a polar or organic solvent, such as, for example, ethanol or methanol, preferably methanol is treated with a suspension of an appropriate catalyst, such as, for example, platinum oxide or platinum or palladium on charcoal. The mixture is then treated with hydrogen until the reaction is complete, and the product of formula $B_o$ is isolated.

The cyclization in Step 5 of the compound of formula $B_o$ to the corresponding oxazolidinone of formula C is carried out by dissolving the compound of formula B in a suitable amount of aprotic organic solvent such as, for example, tetrahydrofuran/toluene or ether/benzene, preferably tetrahydrofuran/toluene and in the presence of a tertiary amine base, such as triethylamine, pyridine, or ethyldi-isopropylamine. The solution is cooled to $-10°$ to 10° C., preferably about 0° C. and an approximately equimolar amount, preferably a slight molar excess of phosgene dissolved in an appropriate inert organic solvent is then added. The mixture containing the compound of formula $B_o$ and phosgene is then stirred for 1 to 4 hours, preferably about 2 hours until the cyclization is essentially complete. The product of formula $C_o$ is then isolated conventionally.

If the thiazolidinone is to be prepared Steps b-1 through b-5 of Reaction Scheme 2 are substituted as a bypass for Step 5.

In step b-1 the compound of formula $B_o$ is dissolved in a polar aprotic organic solvent such as, for example, pyridine. A several-fold molar excess of organic base, such as triethylamine and of carbon disulfide is then added, and the mixture is kept at approximately ambient temperature, preferably about 15° C. to 25° C. This ordinarily will require cooling. The intermediate which results is not isolated, but the reaction mixture is immediately thoroughly cooled to about $-5°$ to 10°, preferably around 0° C., and a several-fold molar excess of benzyl chloride, is added in order to carry out Step b-2. The reaction mixture is kept at the same cold temperature for 10–35 hours, preferably overnight. The resulting product of formula X is then isolated by conventional means.

The compound of formula X is then converted to the cyclic compound of formula Y in the course of Step b-3. In this step, the compound of formula X is added directly to a several-fold molar excess of thionyl chloride (which has been purified as described in *Organic Synthesis* Collective Volume II, page 570) which has been cooled to $-10°$ to 15°, preferably at 0°. The reaction takes place over a period of a half an hour to 2 hours, usually about 1 hour. The excess thionyl chloride is then removed under reduced pressure at slightly above room temperature. The resulting product of formula Y is then extracted and isolated as the hydrochloride salt by conventional means.

The hydrochloride salt of the compound of formula Y is then subjected to Steps b-4 and b-5 to effect the removal of the benzyl thio group and to form the 2-keto-thiazolidanine ring. In carrying out Step b-4, the compound of formula Y is treated with a fairly strong base such as, for example, sodium hydroxide or potassium hydroxide in the presence of a polar solvent such as, for example, ethyl or methyl alcohol or aqueous alcohols. The reaction is carried out with a several-fold molar excess of the base, and at ambient conditions until reaction is complete. The basic solution is then neutralized with acid, and the product recovered. The product will be the unmethylated form of formula $C_s$, since the basic conditions result in the hydrolysis of the methyl ester.

Step b-5 is designed merely to replace the methyl group. In this step, the carboxylic acid form of the compound of formula $C_s$ is dissolved in an aprotic solvent, such as tetrahydrofuran or ether, preferably ether, and treated with a stoichiometric amount or slight excess of diazomethane. The formation of the methyl ester takes place under ambient conditions and is carried to completion, whereupon the product, of formula $C_s$, is isolated by conventional means.

After either Step 5, or, alternatively, Reaction Scheme 2 is completed, the substitution of the hydrogen attached on the ring nitrogen and tautomerization to give the compound of formula D is effected in Step 6. In order to carry out Step 6, the compound of formula E, made slightly basic with a strong organic base, such as, for example, tetramethyl guanidine or Triton B is mixed with a solution of the compound of formula C in a suitable aprotic organic solvent. The compounds of formula C and E are added in approximately equimolar amounts. The solution is then stirred at 10° C. to 40° C., preferably at room temperature for about 24 hours to 75 hours, preferably 45 to 55 hours, whereupon an additional approximately equimolar quantity of the compound of formula E, suitably made basic is added, to assure completion of the reaction. The mixture is then stirred for an additional time period, preferably around 24 hours. The resulting compound of formula D is then isolated if desired.

The compound of formula D is then reduced to the corresponding alcohol or converted to the tertiary alcohol with methyl gringard reagent. In the reduction step, Step 7, the reducing agent, a suitable metal hydride such as, for example, sodium borohydride if $R^2$ is hydrogen or methyl gringard reagent if $R^2$ is methyl, is added to a cold solution of the compound of formula D in a suitable organic solvent. If $R^2$ is hydrogen, a polar organic solvent such as methanol or ethanol may be used; if $R^2$ is methyl, an aprotic organic solvent such as tetrahydrofuran or ether must be used. In any case, equimolar quantities of the reagent and substrate are used. This constitutes, in the case of the metal hydride, a stoichiometric excess of reagent over substrate.

Step 8 is merely the hydrolysis of the methyl ester, if desired, to form the free acid. In this process, the methyl ester prepared in Step 7 is dissolved in an appropriate aqueous or polar organic solvent along with base such as, for example, sodium hydroxide, sodium carbonate, or potassium hydroxide, with stirring, at 0° C. to 30° C. but preferably merely at room temperature for a suitable time period from 1 hour to 40 hours, preferably 18 to 22 hours. When complete, the product is isolated either as the salt or as the free acid.

Other esters and salts may then be made from the free acid form as set forth herein above. Further, if desired, the stereoisomers of the formulas $I_m$ may be resolved into their diastereomeric components by a thin layer chromatography on silicagel, using standard developing solvents such as, for example, ether/hexane: 4/1.

UTILITY AND ADMINISTRATION

The compounds of the invention herein are prostaglandin analogs, and accordingly are useful in inhibiting blood platelet aggregation. The ability of these compounds to do so has been shown by standard in vitro laboratory tests.

Administration of the active compounds and salts described herein can be via any of the accepted modes of administration for prostaglandin type agents which inhibit blood platelet aggregation. While some prostaglandins survive transit through the gastrointestinal tract, the usual method of administration is intravenous diffusion.

The amount of active compound administered will of course, be dependent on the subject being treated, the severity of the affliction, the manner of administration and the judgment of the prescribing physician. However, an effective dosage is in the range of 1–100 ng/kg/min., preferably 5–20 ng/kg/min. For an average 70 kg human, this would amount to 70 ng–7 mg per min., or preferably 0.35–1.4 mg/min., based on intravenous infusion.

Solution type pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s) in an amount effective to alleviate the symptoms of the subject being treated.

If oral administration is desirable, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 1%–95% active ingredient, preferably 25–70%.

PREFERRED EMBODIMENTS

One group of compounds of the present invention which is preferred includes those compounds wherein $R^2$ is hydrogen. Especially preferred among compounds of the above group are those compounds wherein $R^1$ is alkyl or cycloalkyl.

Especially preferred among these are those compounds wherein X is oxygen.

Especially preferred among this group are those compounds and their pharmaceutically acceptable salts and esters selected from the group consisting of:
3-(3-hydroxyoctyl)-4-(6-carboxyhexyl)oxazolidin-2-one;
3-(3-cyclohexyl-3-hydroxypropyl)-4-(6-carboxyhexyl)oxazolidin-2-one;
3-(3-cyclopentyl-3-hydroxypropyl)-4-(6-carboxyhexyl)oxazolidin-2-one;
3-(3-cycloheptyl-3-hydroxypropyl)-4-(6-carboxyhexyl)oxazolidin-2-one.

Another group of preferred embodiments consists of compounds selected from the group consisting of:
3-(5-furan-2-yl)-3-hydroxypentyl)-4-(6-carboxyhexyl)oxazolidin-2-one,
3-(5-(thien-2-yl)-3-hydroxypentyl)-4-(6-carboxyhexyl)oxazolidin-2-one.

The following examples serve to illustrate the invention. They should not be construed as narrowing it, or limiting its scope.

EXAMPLES AND PREPARATIONS

Preparation 1

Preparation of Dimethyl 2-azidoazelate (Step 1)

Soldium azide (4.87 g, 75 mmol) was added to a solution of dimethyl 2-bromoazelate (5.9 g, 20 mmol) prepared according to Auguston, M, et al; *Acta Chim. Acad. Sci. Hung;* 46:85 (1965) in acetonitrile, and the mixture was heated at reflux temperature for 4 h. The solvent was removed in vacuo, dichloromethane (80 ml) was added to the residue, and the mixture was washed with water. The organic phase was dried over sodium sulfate and the solvent was removed in vacuo to give the title compound as an oil (5.1 g, 98% yield).

IR (CHCl$_3$), 2070, 1735 cm$^{-1}$.
NMR (CDCl$_3$) 2.27 (t, 2H); 3.62 (s, 3H); 3.75 (s, 3H); 3.75 (t, 1H).
CIMS(NH$_3$) 275 (M-NH$_4$)$^+$.

Preparation 2

Preparation of 2-Azido-7-methoxycarbonyloctanoic acid (Step 2)

Potassium carbonate (0.414 g, 3 mmol) was added to a solution of the azide prepared in Preparation 1 (0.642 g, 2.5 mmol) in 25% aqueous methanol (20 ml) and the mixture was stirred at room temperature for 3 h. Water (10 ml) was added and the solution was extracted with dichloromethane (40 ml). The aqueous phase was made acidic with oxalic acid and the product was extracted with dichloromethane (4×30 ml). The extract was dried over sodium sulfate and evaporated in vacuo to give the 2-azido-7-methoxycarbonyloctanoic acid as an oil (0.453 g, 74%).

IR (CHCl$_3$), 2080, 1730 cm$^{-1}$.
NMR (CDCl$_3$) 2.30 (t, 2H); 3.64 (s, 3H); 3.85 (t, 1H).
CIMS (NH$_3$) 261 (M-NH$_4$)$^+$.

Preparation 3

Preparation of 2-Azido-8-methoxycarbonyloctan-1-ol (Step 3)

Triethylamine (0.412 g, 4.08 mmol) was added to a stirred solution of the carboxylic acid from Preparation 2 (0.850 g, 3.4 mmol) in anhydrous tetrahydrofuran (40 ml). The mixture was stirred for 5 min., cooled to 0° C., and ethyl chloroformate (0.442 g, 4.08 mmol) was added thereto. After stirring for 1.5 h at 0°, the temperature was left to reach ambient and then the mixture was filtered. The filtrate was added to a mixture of sodium borohydride (0.155 g) and 30% aqueous tetrahydrofuran (5 ml). After 45 min. at room temperature, the mixture was diluted with water (40 ml) and extracted with dichloromethane (4×40 ml). The extract was washed over sodium sulfate and evaporated in vacuo. The residue was subjected to tlc using hexane-ethyl acetate (3:2) as the developing solvent. The 2-azido-8-methoxycarbonyl octan-1-ol was obtained as an oil (0.400 g, 50%).

IR (CHCl$_3$), 3480, 2070, 1730 cm$^{-1}$.
NMR (CDCl$_3$) 1.25–1.70 (m, 10PH); 2.27 (t, 2H); 3.40–3.60 (m, 3H); 3.13 (s, 3H).

Preparation 4

Preparation of 2-Amino-8-methoxycarbonyloctan-1-ol (3) (Step 4)

A solution of the azido alcohol from Preparation 3 (0.200 g, 0.87 mmol) in methanol (20 ml) was added to a prehydrogenated suspension of 10% Pd on charcoal (0.20 g) in methanol (20 ml). The mixture was stirred in an atmosphere of hydrogen until tlc showed that the reduction was complete, [hexane:ethyl acetate (7:3)]. The catalyst was removed by filtration and the filtrate was evaporated in vacuo. Crystallization of the residual solid from methanol-ether gave 2-amino-8-methoxycarbonyloctan-1-ol (3) (0.080 g, 45%), mp 83°–84° C.

IR (CHCl$_3$), 3400, 1730 cm$^-$.
NMR (CDCl$_3$), 1.20–1.60 (m, 10H); 2.26 (t, 2H); 4.02 (m, 6H).
CIMS (NH$_3$) 247 (M-NH$_4$)$^+$.

EXAMPLE 1

Preparation of 4-(6-Methoxycarbonylhexyl)oxazolidin-2-one (Step 5)

Triethylamine (0.505 g, 5 mmol) was added to a solution of 4-(6-methoxycarbonylhexyl)oxazolidin-2-one (1.015 g, 5 mmol) in a 1:1 mixture of tetrahydrofuran and toluene (15 ml). The solution was cooled to 0° C. with stirring and a 20 wt % solution of phosgene in toluene (equivalent to 0.494 g (5.2 mmol) of phosgene) was added. The mixture was stirred for 2 h, water (20 ml) was added, and the product was extracted with dichloromethane (4×40 ml). The extract was dried over sodium sulfate and evaporated in vacuo. The residue was subjected to tlc on silica gel using ethyl acetate-hexane (4:1) as the developing solvent. A crystalline solid 4-(6-methoxycarbonylhexyl)oxazolidin-2-one (0.677 g, 63%) was obtained which was crystallized from dichloromethane-ether-hexane mp 61°–62° C.

IR (CHCl$_3$), 3470, 1760, 1735 cm$^{-1}$.
NMR (CDCl$_3$), 2.28 (t, 2H); 3.63 (s, 3H); 3.70–4.05 (M, 3H).
MS 229 (M+).
Calcd. for C$_{11}$H$_{19}$NO$_4$: C, 57.64; H, 8.29; N, 6.11. Found: C, 57.65; H, 8.22; N, 6.09.

EXAMPLE 2

Preparation of 3-(3-Oxooctyl)-4-(6-methoxycarbonylhexyl)oxazolidin-2-one (Step 6)

Oct-1-en-3-one prepared according to Stetter, H., et al; *Chem. Ber;* 110; 1007 (1977), (1.512 g, 12 mmol) and tetramethylguanidine (0.345 g, 4 mmol) were added to a stirred solution of the oxazolidinone from Example 1 (2.75 g, 12 mmol) in tetrahydrofuran (50 ml). The solution was stirred at room temperature for 48 h at which time additional quantities of the enone (12 mmol) and tetramethylguanidine (4 mmol) were added. After an additional 24 h of agitation the solution was made acidic with acetic acid and diluted with dichloromethane (100 ml). The solution was washed to neutrality with water, dried over sodium sulfate and evaporated in vacuo. The residue was subjected to tlc on silica gel using hexane-ethyl acetate (3:2) as the developing solvent. 3-(3-oxooctyl)-4-(6-methoxcarbonylhexyl)oxazolidin-2-one was obtained as an oil (1.70 g, 40%). In addition, a small amount (0.70 g) of starting material was recovered.

IR (CHCl$_3$), 1745 cm$^{-1}$.
NMR (CDCl$_3$), 0.86 (t, 3H); 2.27 (t, 2H); 2.39 (t, 2H); 2.75 (m, 2H); 3.43 (m, 1H); 3.66 (s, 3H); 3.90 (m,).
MS 355 (M+).

EXAMPLE 3

Preparation of 3-(3-Hydroxyoctyl)-4-(6-methoxycarbonylhexyl)oxazolidin-2-ones (Step 7)

Sodium borohydride (0.170 g, 4.5 mmol) was added with stirring at 0° C. to a solution of 3-(3-oxooctyl)-4-(6-methoxycarbonylhexyl)oxazolidin-2-one (1.59 g, 4.5 mmol) in methanol (25 ml). After 0.5 h at 0° C., the mixture was diluted with dichloromethane (50 ml) and the resulting mixture was washed to neutrality with water. The organic phase was dried over sodium sulfate and evaporated in vacuo. The residual mixture of isomers (1.50 g) was separated by tlc on silica gel using ether-hexane (4:1) as the developing solvent. There was thus obtained the more polar (0.728 g, 46%) and the less polar (0.560 g, 35%) isomers of 3-(3-hydroxyoctyl)-4-(6-methoxycarbonylhexyl)oxazolidin-2-ones both as oils.

The more polar isomer had the following physical constants.

IR (CHCl$_3$), 3470, 1735 cm$^{-1}$.
NMR (CDCl$_3$), 0.88 (t, 3H); 2.27 (t, 2H); 3.35 (m, 2H); 3.63 (s, 3H); 3. (m, 2H); 3.87 (m, 2H).
CIMS(NH$_3$), 375 (M-NH$_4$)+.

The less polar isomer had the following physical constants.

IR (CHCl$_3$), 3490, 1735 cm$^{-1}$.
NMR (CDCl$_3$), 0.87 (t, 3H); 2.28 (t, 2H); 3.05 (m, 2H); 3.50–3.70 (m, 2H); 3.68 (s, 3H); 3.88 (m, 2H).
CIMS(NH$_3$) 375 (M-NH$_4$)+.

EXAMPLE 4

Preparation of Isomeric 3-(3-Hydroxyoctyl)-4-(6-carboxyhexyl)oxazolidin-2-ones (Step 8)

A solution of the more polar methyl ester from 3-(3-hydroxyoctyl)-4-(6-methoxycarbonylhexyl)oxazolidin-2-ones (0.303 g, 0.85 mmol) in methanol (9 ml) and water (1 ml) containing sodium hydroxide (0.068 g, 1.7 mmol) was stirred at room temperature for 10 h. The solution was made acidic (pH 2) by the addition of dilute hydrochloric acid and then most of the methanol was removed in vacuo.

The residue (0.24) g, 82%) was the corresponding carboxylic acid, an oil.

IR (CHCl$_3$), 3450, 1730 cm$^{-1}$.
NMR (CDCl$_3$), 0.88 (t, 3H); 2.32 (t, 2H); 3.37 (t, 2H); 3.50–4.00 (m, 4H).

The less polar ester 3-(3-hydroxyoctyl)-4-(6-methoxycarbonylhexyl)oxazolidin-2-ones was saponified in exactly the same manner as described above. The corresponding carboxylic acid was obtained in 70% yield, as an oil.

IR (CHCl$_3$), 3450, 1725 cm$^{-1}$.
NMR (CDCl$_3$), 0.87 (t, 3H); 2.31 (t, 2H); 3.00–3.20 (m, 2H); 3.50–4.00 (m, 4H).

EXAMPLE 5

Preparation of 3-(3-Cyclohexyl-3-oxopropyl)-4-(6-methoxycarbonylhexyl)oxazolidin-2-one (Step 6)

Vinyl cyclohexyl ketone prepared according to Caldwell, G., et al, *JCS Perk;* 1:495 (1930) (1.38 g, 10 mmol) and tetramethylguanidine (0.570 g, 5 mmol) were added to a solution of the oxazolidinone prepared in Example 1 (2.29 g, 10 mmol) in tetrahydrofuran and the solution was stirred at room temperature for 5 h. At this time an additional quantity of the unsaturated ketone (0.754 g, 5 mmoles) was added and the solution was stirred for a further 4 h. The solution was neutralized with acetic acid, dichloromethane (50 ml) was added and the organic phase was separated and washed with water. The extract was dried over sodium sulfate and evaporated in vacuo to give a residue which was subjected to tlc on silica gel using hexane-ethyl acetate (3:2) as the eluting solvent. The heterocyclic prostaglandin analog was obtained as an oil (1.83 g, 50%):

IR (CHCl$_3$), 1740, 1710 cm$^{-1}$.
NMR (CDCl$_3$), 2.23 (t, 2H); 2.73 (m, 2H); 3.40 (m, 2H); 3.64 (s, 3H); 3.70–4.00 (m, 3H); 4.28 (m, 1H).
CIMS(NH$_3$) 385 (M-NH$_4$)+.

EXAMPLE 6

Preparation of 3-(3-Cyclohexyl-3-hydroxy)propyl-4-(6-methoxycarbonylhexyl)oxazolidin-2-ones (Step 7)

Sodium borohydride (0.038 g, 1 mmol) was added to a stirred solution of the ketone from Example 5 (0.335 g, 1 mmol) in methanol (20 ml) at 0° C. After 1 h, a few drops of 10% hydrochloric acid was added to give a neutral solution and dichloromethane (50 ml) was then added. The organic phase was washed with water, dried over sodium sulfate and evaporated in vacuo. The residue was subjected to tlc on silica gel using hexane:ethyl acetate (1:1) to give the less polar isomer (0.129 g, 38%) and the more polar isomer (0.140 g, 41%) of the heterocyclic prostaglandin analogs as oils.

The less polar isomer had the following physical constants.

IR (CHCl$_3$), 3480, 1730 cm$^{-1}$.

NMR (CDCl$_3$), 2.28 (t, 2H); 3.00-3.40 (m); 3.64 (s, 3H); 3.75-4.00 (m, 3H); 4.38 (m, 1H).

CIMS(NH$_3$) 387 (M-NH$_4$)$^+$.

The more polar isomer had the following physical constants.

IR (CHCl$_3$), 3480, 1735 cm$^{-1}$.

NMR (CDCl$_3$), 2.28 (t, 2H); 3.35 (m, 2H); 3.64 (s, 3H); 3.75-4.00 (m, 3H); 4.35 (m, 1H).

CIMS(NH$_3$) 387 (M-NH$_4$)$^+$.

EXAMPLE 7

Preparation of 3-(3-Cyclohexyl-3-hydroxy)-4-(6-carboxyhexyl)oxazolidin-2-ones (Step 8)

A solution of the less polar methyl ester from Example 6 (0.226 g, 0.61 mmol) in 0.5N methanolic sodium hydroxide (3.7 ml, 1.85 mmol) was stirred at room temperature for 20 h. Water (20 ml) was added and the solution as extracted with dichloromethane (2×20 ml). The aqueous alkaline phase was made acidic to pH 2 with a saturated solution of oxalic acid and the product was extracted with dichloromethane (4×20 ml). The extract was dried over sodium sulfate and evaporated in vacuo. The residue (0.160 g, 73%) was the corresponding pure oily carboxylic acid.

IR (CHCl$_3$), 3460, 1730 cm$^{-1}$.

NMR (CDCl$_3$), 2.34 (t, 2H); 3.30 (m, 2H); 3.70-4.10 (m, 3H); 4.20 (m, 1H).

The more polar ester was hydrolysed in exactly the same manner as described above to give the more polar carboxylic acid as an oil in 79% yield.

IR (CHCl$_3$), 3460, 1735 cm$^{-1}$.

NMR (CDCl$_3$), 2.34 (t, 2H); 3.40 (m, 2H); 3.80-4.10 (m, 3H); 4.22 (m, 1H).

EXAMPLE 8

Preparation of methyl 9-hydroxy-8-(N-dithiocarbobenzyloxyamino)nonanoate (Steps b-1 and b-2)

To 2-amino-8-methoxycarbonyloctan-1-ol (20.0 g) in pyridine (30 ml) triethylamine (1 mol, 16.6 g) and carbon disulphide (1.1 mols, 13.7 g) are added with water cooling. Considerable heat is evolved. The solution is then cooled to 0° and kept at this temperature for 1 hour; benzyl chloride (1 mol, 20.8 g) is added, and the solution kept at 0° overnight. The solution is then poured into 3N sulphuric acid (800 ml) and extracted with ether. The ethereal extract is washed with 3N sulphuric acid and sodium with hydrogen carbonate solution and dried (Na$_2$SO$_4$). After evaporation of the ether, light petroleum (100 ml; b.p. 40°-60°) is added to the residue, which is crystallized in give the product, methyl 9-hydroxy-8-(N-dithiocarbo-benzyloxyamino)-nonanoate.

EXAMPLE 9

Preparation of 4-(methoxycarbonylhexyl)-2-benzylthio-Δ$^2$-thiazoline as the hydrochloride (Step b-3)

Methyl 9-hydroxy-8-(N-dithiocarbobenzyloxyamino)nonanoate from Example 8 is added during 15 minutes to thionyl chloride (20 ml., purified as described in Org. Synth., Coll. Vol. II, p. 570) cooled in ice, and the reaction mixture kept at 0° for 1 hour. Excess thionyl chloride is removed under reduced pressure at 35°. Anhydrous ester (50 ml) is added to the residual oil and the product, 4-(methoxycarbonylhexyl)-2-benzylthio-Δ$^2$-thiazoline, crystallized as the hydrochloride.

EXAMPLE 10

Preparation of 4-(6-methoxycarbonylhexyl)-thiazolidin-2-one (Steps b-4 and b-5)

4-(methoxycarbonylhexyl)-2-benzylthio-Δ$^2$-thiazoline as the hydrachloride, (the product from Example 9), is dissolved in 50 ml ethanol, and 12 ml of N sodium hydroxide is added. The mixture is kept in a stoppered flask for 3 hours. The solution is then neutralized with hydrochloric acid, and the solvent distilled off. The residue is thoroughly extracted with ether, and the ethereal extract evaporated to dryness, leaving a crystalline residue of 4-(6-carboxyhexyl)-thiazolidin-2-one as the free acid.

The residue is then dissolved in 25 ml ether, and an equimolar amount of diazomethane is added. The product, 4-(6-methoxycarbonylhexyl)-thiazolidin-2-one is then recovered and subjected to the procedures as set forth in Examples 2-4 or 5-7.

EXAMPLE 11

Conversion of Free Acid to a Salt 1.0 grams of 3-(3-hydroxyoctyl)-4-(6-carboxyhexyl)oxazolidin-2-one is dissolved in 50 ml of aqueous ethanol, in which 0.5 grams of potassium hydroxide has been dissolved. Ether is added to precipitate the potassium salt of 3-(3-hydroxyoctyl)-4-(6-carboxyhexyl)oxazolidin-2-one.

Substituting for potassium hydroxide in the procedure of the preceding paragraph other bases: e.g. calcium hydroxide, glucosamine, theobromine, or aluminum hydroxide, the corresponding calcium, glucosamine, theobromine, and aluminum salts are prepared.

EXAMPLE 12

Conversion of Free Acid to the Alkyl Ester 1.0 grams of 3-(3-hydroxyoctyl)-4-(6-carboxyhexyl)oxyzoladin-2-one is mixed with 25 ml of isopropanol and 2.0 ml of concentrated hydrochloric acid. The reaction mixture is heated to reflux and refluxed for approximately 1 hour. The resulting isopropyl ester is then distilled from the reaction mixture.

Using other alcohols in place of isopropyl alcohol, such as ethanol or isobutanol, the corresponding ethyl or isobutyl esters respectively may be prepared.

EXAMPLE 13

Conversion of Salt to the Free Acid 1.0 grams of the sodium salt of 3-(3-hydroxyoctyl)-4-(6-carboxyhexyl)-oxazolidin-2-one is dissolved in 50 ml of water to which 10 ml of concentrated sulfuric acid has been added. The resulting 3-(3-hydroxyoctyl)-4-(6-carboxyhexyl)oxyzoladin-2-one is then extracted into two times 50 ml portions of ethyl acetate. The ethyl acetate extracts are dried with magnesium sulfate and evaporated to dryness to give the crystalline 3-(3-hydroxyoctyl)-4-(6-carboxyhexyl)oxazolidin-2-one.

Following the procedure of the preceeding paragraph, other salts and esters of the compounds of the invention may be converted to their corresponding free acid forms.

EXAMPLE 14

Using the Procedure Outlined in Preparations 1 through 4 and Examples 1 through 5, or 8–10 and 2–5; the following compounds of the invention are prepared as the free acids. These may be converted to their salts using the procedure of Example 11 or to the corresponding esters according to the procedure in Example 12. The compounds listed below are thus available in any of the above-mentioned forms: the free acid, the salt, or the alkyl ester.

3-(3-hydroxyhexyl)-4-(6-ethoxycarbonylhexyl)-oxazolidin-2-one;
3-(3-hydroxy-3-cyclopentylpropyl)-4-(6-n-butoxycarbonyl-hexyl)-oxazolidin-2-one;
3-(3-hydroxy-5-(4-ethnylphenyl)pentyl)-4-(6-n-hexoxycarbonylhexyl)-thiazolidin-2-one;
3-(3-hydroxy-4-(3-methoxyphenylthio)butyl)-4-(6-methoxycarbonylhexyl)-thiazolidin-2-one;
3-(3-hydroxy-4-(2-dichorophenoxy)butyl)-4-(6-i-propoxycarbonylhexylthiazolidin-2-one;
3-(3-hydroxy-5-(thien-2-yl)pentyl)-4-(6-carboxyhexyl)-oxazolidin-2-one;
3-(3-hydroxy-4-(furan-3-yloxo)butyl)-4-(6-methoxycarbonylhexyl)-oxazolidin-2-one;
3-(3-hydroxy-4-(thien-3-ylthio)butyl)-4-(6-ethoxycarbonylhexyl)-thiazolidin-2-one;
3-(3-hydroxy-3-cyclopentylpropyl)-4-(6-carboxyhexyl)-oxazolidin-2-one;
3-(3-hydroxy-3-cyclopentylpropyl)-4-(6-methoxycarbonylhexyl)-oxazolidin-2-one;
3-(3-hydroxy-3-cycloheptylpropyl)-4-(6-carboxyhexyl)-oxazolidin-2-one;
3-(3-hydroxy-3-cycloheptylpropyl)-4-(6-methoxycarbonylhexyl)-oxazolidin-2-one;
3-(3-hydroxy)-5-(furan-2-yloxo)pentyl-4-(6-carboxyhexyl)-oxazolidin-2-one;
3-(3-hydroxy)-5-(furan-2-yloxo)pentyl-4-(6-methoxycarbonylhexyl)-oxazolidin-2-one;
3-(3-hydroxy)-5-(furan-2-yl)pentyl-4-(6-methoxycarbonylhexyl)-oxazolidin-2-one;
3-(3-hydroxy)-5-(thien-2-yl)pentyl-4-(6-methoxycarbonylhexyl)-oxazolidin-2-one;

In Examples 15–17 the active ingredient is 3-(3-hydroxyoctyl)-4-(6-carboxyhexyl)oxazolidin-2-one. Other compounds of Formula I and the pharmaceutically acceptable salts thereof may be substituted therein.

EXAMPLE 15

Oral Composition

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 16

Injectable

An injectable preparation buffered to a pH of 7 is prepared having the following composition:

| Ingredients | |
|---|---|
| Active ingredient | 0.02 g |
| KH$_2$PO$_4$ buffer (0.4 M solution) | 2 ml |
| KOH (1 N) | q.s. to pH 7 |
| water (distilled, sterile) | q.s. to 20 ml |

EXAMPLE 17

Injectable

An injectable preparation buffered to a pH of 7 is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

What is claimed:

1. A compound of the formula $$\begin{array}{c} X \diagdown \diagup (CH_2)_6COOH \\ \diagup \diagdown \phantom{xx} R^1 \\ \phantom{xx} \diagdown N-CH_2CH_2\overset{|}{\underset{|}{C}}-R^2 \\ O \phantom{xxxxxxx} OH \end{array} \quad \text{I}$$

TEXT and the pharmaceutically acceptable, non-toxic salts and esters (alkyl, 1–6C) thereof, wherein:
X is S;
R$^1$ is selected from the group consisting of:
(a) alkyl or cycloalkyl of 3–8 carbons,
(b)

$$-CH_2-Z-\!\!\!\bigcirc\!\!\!-Y ,$$

in which Z is O, S or —CH$_2$, and Y is lower alkyl (1–4C), lower alkoxy (1–4C), halo, or —CF$_3$, and (c)

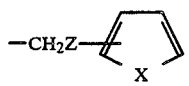

in which Z and X are as herein defined; and R² is hydrogen or methyl.

2. The compound of claim 1 and the pharmaceutically acceptable, non-toxic salts and esters thereof wherein R² is hydrogen.

3. The compound of claim 2 and the pharmaceutically acceptable, non-toxic salts and esters thereof wherein R¹ is alkyl or cycloalkyl.

4. A pharmaceutical composition useful for inhibiting blood platelet aggregation which comprises a therapeutically effective amount of a compound of claim 1 or a pharmaceutically acceptable acid addition salt thereof in admixture with a pharmaceutically acceptable excipient.

5. A method for inhibiting blood platelet aggregation which method comprises administering to a subject in need of such treatment a therapeutically effective amount of, or a pharmaceutical composition containing a therapeutically effective amount of, the compound of claim 1 or a pharmaceutically acceptable acid addition salt thereof.

6. A compound of claim 1, namely 3-(3-hydroxy-3-cyclohexylpropyl)-4-(6-carboxyhexyl)-thiazolidin-2-one.

* * * * *